United States Patent [19]

Dutra et al.

[11] 4,252,554
[45] Feb. 24, 1981

[54] HERBICIDAL ESTER DERIVATIVES OF N-ARYLTHIO-N-PHOSPHONOMETHYL-GLYCINONITRILE

[75] Inventors: Gerard A. Dutra, Ladue; James A. Sikorski, University City, both of Mo.

[73] Assignee: Monsanto Company, St. Louis, Mo.

[21] Appl. No.: 64,676

[22] Filed: Aug. 8, 1979

[51] Int. Cl.$^3$ .......................... A01N 57/14; C07F 9/40
[52] U.S. Cl. .......................................... 71/87; 260/940
[58] Field of Search ............................ 71/87; 260/940

[56] References Cited

U.S. PATENT DOCUMENTS

| | | | |
|---|---|---|---|
| 3,996,040 | 12/1976 | Franz | 71/87 |
| 4,035,177 | 7/1977 | Gaestner | 71/87 |
| 4,067,719 | 1/1978 | Dutra | 71/86 |

FOREIGN PATENT DOCUMENTS 52-142047 of 1977 Japan .

*Primary Examiner*—Catherine L. Mills
*Attorney, Agent, or Firm*—William T. Black; Donald W. Peterson

[57] ABSTRACT

This disclosure relates to novel ester derivatives of N-arylthio-N-phosphonomethylglycinonitrile which are useful as herbicides. This disclosure further relates to herbicidal compositions containing such N-phosphonomethylglycinonitriles and to herbicidal methods employing such compounds and compositions.

18 Claims, No Drawings

HERBICIDAL ESTER DERIVATIVES OF N-ARYLTHIO-N-PHOSPHONOMETHYL-GLYCINONITRILE

This invention relates to novel ester derivatives of N-arylthio-N-phosphonomethylglycinonitrile which are useful as herbicides. This invention further relates to herbicidal compositions containing such N-phosphonomethylglycinonitriles and to herbicidal methods employing such compounds and compositions.

U.S. Pat. No. 4,067,719 discloses N-phosphonomethylglycinonitriles of the formula

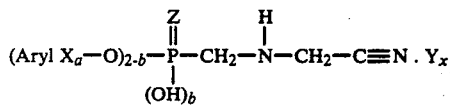

wherein (Aryl) is selected from phenyl, napthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 1, provided that x must be zero when b is 1, as well as a process for producing such compounds. These N-phosphonomethylglycinonitriles are useful as herbicides.

U.S. Pat. No. 4,008,296 describes ester derivatives of N-phosphonomethylglycinonitrile having the formula

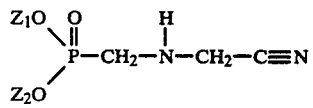

wherein $Z_1$ and $Z_2$ each represent an alkyl radical of from 1 to 6 carbon atoms; which are useful as herbicides.

Japanese L.O.P. No. 142047/1977 discloses phenylcyanomethylaminomethylphosphonates of the formula

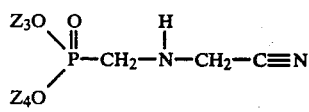

wherein $Z_3$ is hydrogen or phenyl and $Z_4$ is phenyl. Japanese L.O.P. No. 93323/1974 describes the preparation of N-(diethylphosphonomethyl)aminoacetonitrile.

The compounds of the present invention are represented by the formula

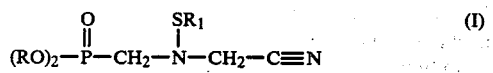

wherein R is phenyl, naphthyl or biphenylyl or phenyl, naphthyl or biphenylyl substituted with from one to three substituents independently selcted from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from one to three substituents independently selected from the class consisting of lower alkyl, lower alkoxy, halogen, trifluoromethyl and nitro.

It is preferred that R is phenyl or substituted phenyl. Also, it is preferred that the substituted phenyl groups represented by R or $R_1$ contain one or two substituents.

Illustrative of the substituted phenyl groups which R and $R_1$ represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of the substituted biphenylyl groups represented by R include methylbiphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have up to four carbon atoms in a straight or branched chain, such as, for example, methyl, ethyl, propyl, isopropyl, butyl, isobutyl, sec-butyl, and t-butyl.

In accordance with the present invention, the N-phosphonomethylglycinonitriles of formula (I) are prepared by reacting a compound of the formula

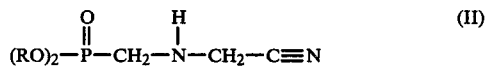

wherein R is above defined; in an aprotic solvent, with a sulfenyl chloride of the formula

wherein $R_1$ is above defined; in the presence of a hydrogen chloride acceptor.

It has been found that the reaction temperature may range from 0° to 100° C. For ease of reaction and recovery of product, it is preferred to conduct the process of the present invention within a range of 0° to 30° C.

In preparing the novel glycinonitriles of formula (I), the ratio of reactants is not narrowly critical. For best results, however, for each mole of a compound of formula (II), one should employ one mole of a sulfenyl chloride of formula (III) to produce one mole of a glycinonitrile compound of formula (I). It is preferred to employ an excess of a sulfenyl chloride of formula (III) for ease of reaction and maximum yield of product. The hydrogen chloride acceptor is preferably used in stoichiometric excess to insure completeness of reaction.

The hydrogen chloride acceptor is an amine, preferably a tertiary amine, which will not react with the reactants or products formed. Examples of tertiary amine hydrogen chloride acceptors include trimethylamine, triethylamine, tributylamine, trihexylamine, 1,5-diazabicyclo-[5.4.0]-undec-5-ene, pyridine, quinoline and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, tetrahydrofuran, cyclohexane, methylcyclohexane, hexane, octane, dioxane, ethyl ether and the like.

While the processes of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

To a mixture of N-diphenoxyphosphinylmethylglycinonitrile (10.0 g; 0.033 mol.) and triethylamine (3.35 g; 0.033 mol.) in 100 ml. of toluene was added 4-chlorophenylsulfenyl chloride (5.91 g; 0.033 mol.). The reaction mixture was stirred for 16 hours at 25° C., filtered and the filtrate was concentrated to yield a yellow oil. The yellow oil was chromatographically purified employing a silica gel column and a 1:1 mixture (by volume) of cyclohexane: ethyl acetate as an eluent to yield N-[(4-chlorophenyl)thio]-N-[diphenoxyphosphinylmethyl]glycinonitrile (2.1 g; 14.3% yield) as a yellow oil ($n_D^{25}$ = 1.5862) having the following analysis:

Calculated: C, 56.70; H, 4.08; N, 6.30, Found: C, 57.23; H, 4.13; N, 6.30.

EXAMPLE 2

To a mixture of N-diphenoxyphosphinylmethylglycinonitrile (10.0 g; 0.033 mol.) and triethylamine (3.35 g; 0.033 mol.) in 100 ml. of toluene was added 4-methylphenylsulfenyl chloride (5.23 g; 0.033 mol.). The reaction mixture was stirred for 16 hours at 25° C., filtered and the filtrate was concentrated to yield a crude product. The crude product was chromatographically purified employing a silica gel column and a 1:1 mixture (by volume) of cyclohexane: ethyl acetate as an eluent to yield N-[(4-methylphenyl)thio]-N-[diphenoxyphosphinylmethyl]glycinonitrile (3.3 g; 23.6% yield) as a yellow oil ($n_D^{25}$ = 1.5878) having the following analysis:

Calculated: C, 62.25; H, 4.99; N, 6.60, Found: C, 62.41; H, 4.82; N, 6.25.

EXAMPLE 3

To a mixture of N-di(4-methoxyphenyl)phosphinylmethylglycinonitrile (3.0 g; 0.008 mol.) and triethylamine (0.8 g; 0.008 mol.) in 100 ml. of toluene was added 4-chlorophenylsulfenyl chloride (1.48 g; 0.003 mol.). The reaction mixture was stirred for 16 hours at 25° C., filtered and the filtrate was concentrated to yield a crude product. The crude product was chromatographically purified employing a silica gel column and a 3:2 mixture (by volume) of cyclohexane: ethyl acetate as an eluent to yield N-[(4-chlorophenyl)thio]-N-[di-(4-methoxyphenyl)phosphinylmethyl]glycinonitrile (1.17 g; 29.3% yield) as an orange oil ($n_D^{25}$ = 1.5892) having the following analysis:

Calculated: C, 54.71; H, 4.39; N, 5.55, Found: C, 54.56; H, 4.42; N, 5.52.

EXAMPLE 4

To a mixture of N-di(4-methoxyphenyl)phosphinylmethylglycinonitrile (3.0 g; 0.008 mol.) and triethylamine (0.8 g; 0.008 mol.) in 100 ml. of toluene was added 4-methylphenylsulfenyl chloride (1.27 g; 0.008 mol.). The reaction mixture was stirred for 16 hours at 25° C., filtered and the filtrate was concentrated to yield a yellow oil. The yellow oil was chromatographically purified employing a silica gel column and a 3:2 mixture (by volume) of cyclohexane: ethyl acetate as an eluent to yield N-[(4-methylphenyl)thio]-N-[di-(4-methoxyphenyl)-phosphinylmethyl]glycinonitrile (1.48 g; 36.6% yield) as a colorless oil ($n_D^{25}$ = 1.5805) having the following analysis:

Calculated: C, 59.50; H, 5.20; N, 5.73. Found: C, 59.24; H, 5.27; N, 5.69.

EXAMPLE 5

To a mixture of N-di(4-methoxyphenyl)phosphinylmethylglycinonitrile (3.28 g; 0.008 mol.) and triethylamine (1.34 g; 0.013 mol.) in 200 ml. of toluene was added phenylsulfenyl chloride (1.86 g; 0.013 mol.). The reaction mixture was stirred for 64 hours at 26° C., filtered and the filtrate was concentrated to yield a crude product. The crude product was chromatographically purified employing a silica gel column and a 3:2 mixture (by volume) of cyclohexane: ethylacetate as an eluent to yield N-phenylthio-N-[di-(4-methoxyphenylphosphinylmethyl]glycinonitrile (1.59 g; 42.3% yield) as a yellow oil ($n_D^{25}$ = 1.5851) having the following analysis:

Calculated: C, 58.72; H, 4.93; N, 5.95, Found: C, 58.57; H, 4.97; N, 5.94.

EXAMPLE 6

To a mixture of N-diphenoxyphosphinylmethylglycinonitrile (10.0 g; 0.033 mol.) and triethylamine (3.35 g; 0.033 mol.) in 100 ml. of toluene was added (3-trifluoromethylphenyl)sulfenyl chloride (7.01 g; 0.033 mol.). The reaction mixture was stirred for 16 hours at 25° C., filtered and the filtrate was concentrated to yield a crude product. The crude product was chromatographically purified employing a silica gel column and a 3:2 mixture (by volume) of cyclohexane:ethylacetate as an eluent to yield N-[(3-trifluoromethylphenyl)thio]-N-[diphenoxyphosphinylmethyl]glycinonitrile (7.3 g; 46.2% yield) as a yellow oil ($n_D^{25}$ = 1.5506) having the following analysis:

Calculated: C, 55.23; H, 3.79; N, 5.86, Found: C, 55.10; H, 3.82; N, 5.79.

EXAMPLE 7

To a mixture of N-diphenoxyphosphinylmethylglycinonitrile (10.0 g; 0.033 mol.) and triethylamine (3.34 g; 0.033 mol.) in 100 ml. of toluene was added 4-methoxyphenylsulfenyl chloride (6.4 g; 0.033 mol.). The reaction mixture was stirred for 16 hours at 25° C., and then concentrated to yield a crude product. The crude product was chromatographically purified employing a silica gel column and a 3:2 mixture (by volume) of cyclohexane: ethylacetate as an eluent to yield N-[(4-methoxyphenyl)thio]-N-[diphenoxyphosphinylmethyl]-glycinonitrile (8.75 g; 61% yield) as an orange oil ($n_D^{23}$ = 1.5699) having the following analysis:

Calculated: C, 59.99; H, 4.81; N, 6.36, Found: C, 59.76; H, 4.81; N, 6.28.

EXAMPLE 8

To a mixture of N-diphenoxyphosphinylmethylglycinonitrile (10.0 g; 0.033 mol.) and triethylamine (3.35 g; 0.033 mol.) in 100 ml. of toluene was added phenyl sulfenyl chloride (4.77 g; 0.033 mol.). The reaction mixture was stirred for 16 hours at 25° C., filtered and the filtrate was concentrated to yield an orange oil. The orange oil was washed with carbon tetrachloride and then chromatographically purified employing a silica gel column and a 3:2 mixture (by volume) of cyclohexane:ethylacetate as an eluent to yield N-phenylthio-N-[diphenoxyphosphinylmethyl]glycinonitrile (4.00 g; 29.5% yield) as an yellow oil ($n_D^{25} = 1.5850$) having the following analysis:

Calculated: C, 61.45; H, 4.67; N, 6.83, Found: C, 61.64; H, 4.62; N, 6.75.

EXAMPLE 9

A mixture of N-[diphenoxyphosphinylmethyl]glycinonitrile (15.1 g; 0.05 mol.) in 150 ml. of toluene was cooled to 0° C. To the cooled mixture was added triethylamine (5.06 g; 0.05 mol.) A solution of (2,4-dinitrophenyl)sulfenyl chloride (11.73 g; 0.05 mol.) in 200 ml. of toluene was added to the reaction mixture at a rate such that the temperature of the reaction did not exceed 10° C. The reaction mixture was stirred for 1 hour at 5° C. then for 20 hours at 25° C., and subsequently filtered to yield a yellow solid. The yellow solid was purified upon recrystallization from chloroform to yield N-[(2,4-dinitrophenyl)thio]-N-[diphenoxyphosphinylmethyl]glycinonitrile (2.70 g; 10.8% yield) as a yellow solid having a melting point of 147°–149° C. and the following analysis:

Calculated: C, 50.40; H, 3.42; N, 11.20; S, 6.41, Found: C, 50.28; H, 3.46; N, 11.17; S, 6.42.

EXAMPLE 10

A mixture of N-diphenoxyphosphinylmethylglycinonitrile (15.1 g; 0.05 mol.) in 150 ml. of benzene was cooled to 10° C. To the cooled mixture was added triethylamine (5.06 g; 0.05 mol.). A solution of 2-nitrophenylsulfenyl chloride (9.48 g; 0.05 mol.) in 100 ml. of benzene was added to the reaction mixture at a rate such that the temperature of the reaction did not exceed 10° C. When the addition was complete, the reaction mixture was stirred at 10° C. for 15 minutes then at 25° C. for 5 hours, after which time the reaction mixture was filtered and the filtrate concentrated to yield a red oil. To the red oil was added 50 ml. of carbon tetrachloride producing a yellow oil which was chromatographically purified employing a silica gel column and a 3:2 mixture (by volume) of cyclohexane:ethylacetate as an eluent to yield N-[(2-nitrophenyl)thio]-N-[diphenoxyphosphinylmethyl]glycinonitrile (1.5 g; 6.6% yield) as a yellow oil ($n_D^{25} = 1.6172$) having the following analysis:

Calculated: C, 53.79; H, 4.19; N, 8.96; S, 6.84, Found: C, 53.83; H, 3.93; N, 8.89; S, 6.88.

EXAMPLE 11

Under a nitrogen atmosphere, triethylamine (2.6 g; 0.026 mol.) was combined with N-[di-(3-methyl-4-chloro-phenoxy)-phosphinylmethyl]glycinonitrile (10.3 g; 0.026 mol) in 100 ml. of toluene. To the reaction mixture was added 4-methylphenylsulfenyl chloride (4.1 g; 0.026 mol.) and the resulting mixture was stirred for 21 hours at 25° C. The reaction mixture was washed with sodium hydroxide, water, dried over magnesium sulfate, filtered and the filtrate concentrated to yield a brown oil. The brown oil was chromatographically purified employing a silica gel column and a 3:2 mixture (by volume) of cyclohexane:ethylacetate as an eluent to yield N-[(4-methylphenyl)thio]-N-[di-(3-methyl-4-chlorophenoxy)phosphinylmethyl]glycinonitrile (1.86 g; 13.7% yield) as a brown solid having a melting point of 60°–63° C. and the following analysis:

Calculated: C, 55.29; H, 4.45; N, 5.37; S, 6.15, Found: C, 55.16; H, 4.52; N, 5.29; S, 6.08.

EXAMPLE 12

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed in a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| A | Canada Thistle* | K | Barnyardgrass |
| --- | --- | --- | --- |
| B | Cocklebur | L | Soybean |
| C | Velvetleaf | M | Sugar Beet |

-continued

| | | | |
|---|---|---|---|
| D | Morningglory | N | Wheat |
| E | Lambsquarters | O | Rice |
| F | Smartweed | P | Sorghum |
| G | Yellow Nutsedge* | Q | Wild Buckwheat |
| H | Quackgrass* | R | Hemp Sesbania |
| I | Johnsongrass* | S | Panicum Spp |
| J | Downy Brome | T | Crabgrass |

A dash in the tables indicate that the particular species was absent in the test.

tive propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans

TABLE I

| Compound of Example No. | WAT | kg/h | Plant Species | | | | | | | | | | |
|---|---|---|---|---|---|---|---|---|---|---|---|---|---|
| | | | A | B | C | D | E | F | G | H | I | J | K |
| 1 | 4 | 11.2 | 2 | 3 | 2 | 2 | 4 | 4 | 2 | 2 | 4 | 2 | 3 |
| | 4 | 5.6 | 1 | 3 | 3 | 2 | 3 | 4 | 1 | 3 | 4 | 3 | 3 |
| 2 | 4 | 11.2 | 2 | 3 | 2 | 2 | 3 | 2 | 2 | 0 | 3 | 2 | 3 |
| | 4 | 5.6 | 1 | 2 | 1 | 2 | 4 | 2 | 2 | 1 | 3 | 1 | 2 |
| 3 | 4 | 11.2 | 2 | 2 | 0 | 1 | 3 | 3 | 2 | 0 | 0 | 0 | 2 |
| | 4 | 5.6 | 2 | 1 | 0 | 2 | 1 | 2 | 2 | 1 | 0 | 0 | 2 |
| 4 | 4 | 11.2 | 1 | 3 | 1 | 2 | 3 | 1 | 2 | 1 | 3 | 1 | 2 |
| | 4 | 5.6 | 1 | 1 | 0 | 2 | 2 | 1 | 0 | 0 | 3 | 1 | 2 |
| 5 | 4 | 11.2 | 1 | 2 | 1 | 2 | 1 | 1 | 0 | 1 | 3 | 1 | 2 |
| | 4 | 5.6 | 4 | 2 | 1 | 2 | 4 | 2 | 1 | 1 | 3 | 1 | 2 |
| 6 | 4 | 11.2 | 1 | 3 | 1 | 2 | 4 | 4 | 2 | 2 | 4 | 1 | 3 |
| | 4 | 5.6 | 2 | 2 | 1 | 2 | 3 | 4 | 2 | 1 | 3 | 1 | 3 |
| 7 | 4 | 11.2 | 2 | 4 | 3 | 3 | 4 | 4 | 1 | 2 | 3 | 2 | 3 |
| | 4 | 5.6 | 2 | 4 | 3 | 3 | 4 | 4 | 3 | 1 | 2 | 2 | 3 |
| 8 | 4 | 11.2 | — | 3 | 3 | 2 | 2 | 3 | 2 | 2 | 4 | 2 | 3 |
| | 4 | 5.6 | — | 2 | 1 | 2 | 3 | 4 | 2 | 1 | 4 | 1 | 3 |
| 9 | 4 | 11.2 | 2 | 3 | 1 | 2 | 2 | 2 | 2 | 0 | 3 | 0 | 3 |
| | 4 | 5.6 | 1 | 2 | 2 | 2 | 3 | 4 | 1 | 0 | 3 | 0 | 2 |
| 10 | 4 | 11.2 | 2 | 4 | 1 | 2 | 3 | 1 | 1 | 0 | 3 | 2 | 2 |
| 11 | 4 | 11.2 | — | 1 | 0 | 1 | 3 | 0 | 1 | 0 | 1 | 0 | 1 |
| | 4 | 5.6 | — | 1 | 0 | 1 | 1 | 0 | 0 | 0 | 0 | 0 | 0 |

TABLE II

| Compound of Example No. | WAT | kg/h | Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 1 | 4 | 5.6 | 2 | 1 | 2 | 3 | 4 | 3 | 2 | — | 1 | — | 4 | 2 | 3 | 3 | 4 | 4 |
| | | 1.12 | 1 | 0 | 0 | 1 | 3 | 2 | 1 | 2 | 1 | 2 | 2 | 1 | 1 | 2 | 3 | 3 |
| | | 0.28 | 1 | 0 | 0 | 0 | 2 | 2 | 1 | 1 | 0 | 3 | 1 | 0 | 0 | 0 | 2 | 1 |
| 2 | 4 | 5.6 | 2 | 2 | 2 | 4 | 4 | 4 | 4 | 3 | — | 4 | 3 | 3 | 3 | 3 | 4 | 3 |
| | 4 | 1.12 | 1 | 0 | 0 | 0 | 1 | 2 | 0 | 2 | 0 | 4 | 1 | 1 | 0 | 1 | 1 | 1 |
| 3 | 4 | 5.6 | 2 | 2 | 1 | 1 | 3 | 3 | 2 | 3 | 1 | — | 3 | 1 | 1 | 3 | 3 | 3 |
| | 4 | 1.12 | 1 | 0 | 0 | 0 | 1 | 2 | 0 | 2 | 0 | 4 | 1 | 1 | 0 | 1 | 1 | 1 |
| 4 | 4 | 5.6 | 2 | 1 | 2 | 1 | 2 | — | 2 | 3 | 2 | 4 | 4 | 3 | 1 | 2 | 3 | 3 |
| | 4 | 1.12 | 1 | 2 | 2 | 1 | 1 | 2 | 2 | 2 | 2 | 3 | 3 | 2 | 2 | 3 | 3 | 3 |
| | 4 | 0.28 | 1 | 0 | 0 | 0 | 1 | — | 0 | 1 | 0 | 1 | 1 | 0 | 0 | 1 | 1 | 1 |
| | 2 | 0.053 | 0 | 0 | 0 | 0 | 0 | 0 | 0 | 0 | 0 | 0 | 0 | 0 | 0 | 0 | 0 | 0 |
| 6 | 4 | 5.6 | 3 | 2 | 1 | 4 | 3 | 3 | 2 | 3 | 4 | 2 | 3 | 1 | 2 | 3 | 3 | 3 |
| | 4 | 1.12 | 1 | 1 | 1 | 0 | 2 | 2 | 1 | 2 | 1 | — | 2 | 1 | 0 | 1 | 2 | 2 |
| | 4 | 0.28 | 1 | 0 | 0 | 0 | 0 | 1 | 0 | 1 | 0 | 1 | 0 | 0 | 0 | 0 | 0 | 0 |
| 7 | 4 | 5.6 | 2 | 1 | 3 | 3 | 3 | 3 | 1 | 3 | — | 4 | 4 | 3 | 3 | 4 | 4 | — |
| | 4 | 1.12 | 1 | 0 | 1 | 4 | 3 | 2 | 0 | 2 | — | 4 | 1 | 1 | 1 | 4 | 3 | — |
| | 4 | 0.28 | 0 | 0 | 0 | 1 | 2 | 1 | 0 | 1 | 0 | 1 | 2 | 0 | 1 | 1 | 2 | — |
| | 2 | 0.053 | 0 | 0 | 0 | 0 | 0 | 0 | 0 | 0 | 0 | 0 | 0 | 0 | 0 | 0 | 1 | — |
| 8 | 4 | 5.6 | 3 | 4 | 2 | 2 | 4 | 4 | 4 | 4 | 4 | 4 | 4 | 3 | 3 | 3 | 3 | 4 |
| | 4 | 1.12 | 1 | 1 | 1 | 2 | 4 | 2 | 2 | 2 | 1 | 3 | 1 | 2 | 2 | 1 | 3 | 3 |
| | 4 | 0.28 | 1 | 1 | 1 | 2 | 4 | 2 | 2 | 2 | 1 | 3 | 1 | 2 | 2 | 1 | 3 | 3 |
| 9 | 4 | 5.6 | 2 | 2 | 2 | 1 | 4 | 3 | 2 | 2 | 1 | — | 1 | 1 | 1 | 2 | 3 | 3 |
| | 4 | 1.12 | 1 | 0 | 0 | 0 | 3 | 1 | 2 | 2 | 0 | 2 | 1 | 1 | 1 | 2 | 2 | 2 |
| | 2 | 0.28 | 0 | 0 | 0 | 0 | 1 | 1 | 0 | 1 | — | 1 | 0 | 0 | 0 | — | 0 | 1 |
| 10 | 4 | 5.6 | 2 | 1 | 1 | 1 | 4 | 3 | 3 | — | 4 | 4 | 1 | 1 | 3 | 3 | 3 | 3 |
| | 4 | 1.12 | 0 | 0 | 0 | 0 | 1 | 0 | 0 | 1 | 0 | 4 | 0 | 0 | 0 | 0 | 2 | 3 |
| | 2 | 0.28 | 0 | 0 | 0 | 0 | 1 | 0 | 0 | 1 | 0 | 1 | 0 | 0 | 0 | 0 | 2 | 2 |

EXAMPLE 13

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegeta- to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III and IV.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | Plant Species | | | | | | | | | | |
|---|---|---|---|---|---|---|---|---|---|---|---|---|---|
| | | | A | B | C | D | E | F | G | H | I | J | K |
| 1 | 2 | 11.2 | 3 | 0 | 0 | 2 | 2 | 0 | 1 | 2 | 3 | 0 | 1 |
| 2 | 2 | 11.2 | 3 | 0 | 0 | 0 | 3 | 0 | 0 | 1 | 2 | 0 | 0 |
| 3 | 2 | 11.2 | 0 | 0 | 0 | 0 | 1 | 0 | 0 | 3 | 0 | 0 | 0 |
| 4 | 2 | 11.2 | 0 | 0 | 0 | 0 | 1 | 0 | 0 | 0 | 0 | 0 | 1 |
| 5 | 2 | 11.2 | 1 | 0 | 0 | 0 | 1 | 0 | 0 | 0 | 0 | 0 | 1 |
| 6 | 2 | 11.2 | 3 | 0 | 0 | 0 | 3 | 1 | 0 | 2 | 3 | 1 | 0 |
| 7 | 2 | 11.2 | 3 | 0 | 1 | 0 | 3 | 0 | 1 | 1 | 3 | 1 | 0 |
| 8 | 4 | 11.2 | 2 | 1 | 0 | 0 | 3 | 1 | 3 | 2 | 3 | 0 | 1 |
| 9 | 2 | 11.2 | 1 | 0 | 0 | 1 | 3 | 0 | 0 | 0 | 1 | 0 | 3 |
| 10 | 2 | 11.2 | 0 | 0 | 0 | 0 | 0 | 0 | 0 | 0 | 0 | 0 | 0 |
| 11 | 2 | 11.2 | — | 0 | 0 | 1 | 0 | 0 | 0 | 0 | 0 | 0 | 0 |

TABLE IV

| Compound of Example No. | WAT | kg/h | Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 8 | 2 | 11.2 | 0 | 0 | 0 | 0 | 3 | 0 | 1 | 0 | 0 | 3 | 1 | 0 | 0 | 1 | 1 | 3 |
| | 2 | 5.6 | 0 | 0 | 0 | 0 | 2 | 0 | 0 | 0 | 0 | 3 | 1 | 0 | 0 | 1 | 1 | 3 |
| | 2 | 1.12 | 0 | 0 | 0 | 0 | 0 | 0 | 0 | 0 | 0 | 0 | 0 | 0 | 0 | 0 | 0 | 1 |
| ·9 | 2 | 5.6 | 0 | 0 | 0 | 0 | 0 | 0 | 0 | 0 | 0 | 0 | 0 | 0 | 0 | 0 | 0 | 0 |
| | 2 | 1.12 | 0 | 0 | 0 | 0 | 0 | 0 | 0 | 0 | 0 | 0 | 0 | 0 | 0 | 0 | 0 | 0 |

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing plants or seeds or vegetative propagules, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycinonitrile employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula

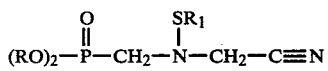

wherein R is phenyl, naphthyl or biphenylyl or phenyl, naphthyl or biphenylyl substituted with from one to three substituents independently selected from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from one to three substituents independently selected from the class consisting of lower alkyl, lower alkoxy, halogen, trifluoromethyl and nitro.

2. A compound according to claim 1 wherein R is phenyl.

3. A compound according to claim 2 wherein $R_1$ is phenyl substituted with from one to three substituents independently selected from the class consisting of lower alkyl, lower alkoxy, halogen and trifluoromethyl.

4. A compound according to claim 3 wherein the compound is N-[(4-methoxyphenyl)thio]-N-[diphenoxyphosphinylmethyl]glycinonitrile.

5. A compound according to claim 3 wherein the compound is N-[(4-chlorophenyl)thio]-N-[diphenoxyphosphinylmethyl]glycinonitrile.

6. A compound according to claim 2 wherein the compound is N-phenylthio-N-[diphenoxyphosphinylmethyl]-glycinonitrile.

7. A herbicidal composition comprising an inert adjuvant and a herbicidally effective amount of a compound of the formula

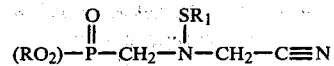

wherein R is phenyl, naphthyl or biphenyl or phenyl, naphthyl or biphenylyl substituted with from one to three substituents independently selected from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from one to three substituents independently selected from the class consisting of lower alkyl, lower alkoxy, halogen, trifluoromethyl and nitro.

8. A composition according to claim 7 wherein R is phenyl.

9. A composition according to claim 8 wherein $R_1$ is phenyl substituted with from one to three substituents independently selected from the class consisting of lower alkyl, lower alkoxy, halogen and trifluoromethyl.

10. A composition according to claim 9 wherein the compound is N-[(4-methoxyphenyl)thio]-N-[diphenoxyphosphinylmethyl]glycinonitrile.

11. A composition according to claim 9 wherein the compound is N-[(4-chlorophenyl)thio]-N-[diphenoxyphosphinylmethyl]glycinonitrile.

12. A composition according to claim 8 wherein the compound is N-phenylthio-N-[diphenoxyphosphinylmethyl]glycinonitrile.

13. A method of controlling undesired plants which comprises contacting said plants or plant growth medium with a herbicidal amount of a compound of the formula

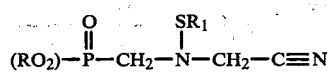

wherein R is phenyl, naphthyl or biphenylyl or phenyl, naphthyl or biphenylyl substituted with from one to three substituents independently selected from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from one to three substituents independently selected from the class consisting of lower alkyl, lower alkoxy, halogen, trifluoromethyl and nitro.

14. A method according to claim 13 wherein R is phenyl.

15. A method according to claim 14 wherein $R_1$ is phenyl substituted with from one to three substituents independently selected from the class consisting of lower alkyl, lower alkoxy, halogen and trifluoromethyl.

16. A method according to claim 15 wherein the compound is N-[(4-methoxyphenyl)thio]-N-[diphenoxyphosphinylmethyl]glycinonitrile.

17. A method according to claim 15 wherein the compound is N-[(4-chlorophenyl)thio]-N-[diphenoxyphosphinylmethyl]glycinonitrile.

18. A method according to claim 14 wherein the compound is N-phenylthio-N-[diphenoxyphosphinylmethyl]-glycinonitrile.

* * * * *

UNITED STATES PATENT AND TRADEMARK OFFICE
CERTIFICATE OF CORRECTION

PATENT NO. : 4,252,554

DATED : February 24, 1981

INVENTOR(S) : Dutra, et al

It is certified that error appears in the above-identified patent and that said Letters Patent are hereby corrected as shown below:

Column 7, line 9 following the legend insert

--* - Established from vegetative propagules--

Signed and Sealed this

Fifteenth Day of September 1981

[SEAL]

Attest:

GERALD J. MOSSINGHOFF

Attesting Officer

Commissioner of Patents and Trademarks